United States Patent
Yamaguchi et al.

(10) Patent No.: US 7,651,538 B2
(45) Date of Patent: Jan. 26, 2010

(54) HAIR DYE COMPOSITION

(75) Inventors: Masakazu Yamaguchi, Sumida-ku (JP); Dominic Pratt, Darmstadt (DE); Yasuhiro Ishiwata, Minamiashigara (JP)

(73) Assignees: Kao Corporation, Tokyo (JP); Fujifilm Corporation, Tokyo (JP)

( * ) Notice: Subject to any disclaimer, the term of this patent is extended or adjusted under 35 U.S.C. 154(b) by 38 days.

(21) Appl. No.: 11/816,422

(22) PCT Filed: Feb. 10, 2006

(86) PCT No.: PCT/JP2006/302336

§ 371 (c)(1), (2), (4) Date: Aug. 16, 2007

(87) PCT Pub. No.: WO2006/087970

PCT Pub. Date: Aug. 24, 2006

(65) Prior Publication Data

US 2009/0056038 A1 Mar. 5, 2009

(30) Foreign Application Priority Data

Feb. 18, 2005 (JP) ............................. 2005-041788

(51) Int. Cl.
*A61Q 5/10* (2006.01)
*C07D 275/02* (2006.01)

(52) U.S. Cl. .................. 8/405; 8/406; 8/437; 8/565; 8/567; 8/568; 8/570; 8/571; 8/575; 8/587; 548/206

(58) Field of Classification Search .............. 8/405, 8/406, 437, 565, 567, 568, 570, 571, 575, 8/587; 548/206
See application file for complete search history.

(56) References Cited

FOREIGN PATENT DOCUMENTS

| JP | 56 55455 | 5/1981 |
| JP | 58 179267 | 10/1983 |
| JP | 2000 280630 | 10/2000 |
| JP | 2002-280630 | * 10/2000 |
| JP | 2003 342139 | 12/2003 |
| JP | 2004 107343 | 4/2004 |
| JP | 2006-016471 | * 1/2006 |
| WO | 2006 004134 | 1/2006 |
| WO | WO 2006/004134 A1 | * 12/2006 |

OTHER PUBLICATIONS

STIC Search Report dated Dec. 29, 2008.*
U.S. Appl. No. 11/722,750, filed Jun. 25, 2007, Yamaguchi, et al.

* cited by examiner

*Primary Examiner*—Eisa B Elhilo
(74) *Attorney, Agent, or Firm*—Oblon, Spivak, McClelland, Maier & Neustadt, L.L.P.

(57) ABSTRACT

A hair dye composition containing an azo dye (1) or a salt thereof,

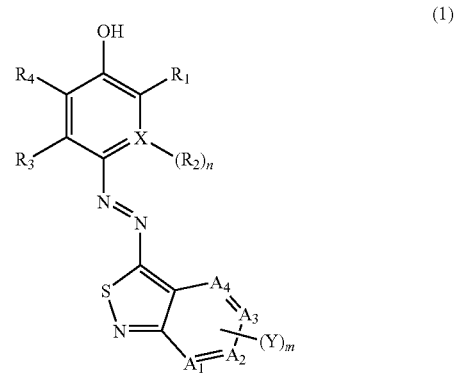

(wherein $R_1$ to $R_4$ represents H, aliphatic hydrocarbon group, aryl group, halogen atom, acyl group, cyano group, acylamino group, or the like, wherein $R_1$ and $R_2$, and/or $R_3$ and $R_4$ may be coupled to form a 5- or 6-membered ring; X represents C or N, with the proviso that when X represents C, n stands for 1, and when X represents N, n stands for 0; $A_1$, $A_2$, $A_3$ and $A_4$ each represents N or represents C substituted by Y or having H, with the proviso that at least one of $A_1$, $A_2$, $A_3$ and $A_4$ is a nitrogen atom; and Y represents a substituent with the proviso that m stands for an integer from 0 to 3).

13 Claims, No Drawings

HAIR DYE COMPOSITION

FIELD OF THE INVENTION

The present invention relates to a hair dye composition containing an azo dye.

BACKGROUND OF THE INVENTION

Hair dyes can be classified by the dye to be used or by whether they have any bleaching action on melanin or not. Typical examples include a two-part permanent hair dye composed of a first part containing an alkali agent, an oxidation dye and optionally a direct dye such as a nitro dye and a second part containing an oxidizing agent; and a one-part semi-permanent hair dye containing an organic acid or an alkali agent, and at least one direct dye such as an acid dye, basic dye or nitro dye.

The above-described two-part permanent hair dye however has drawbacks that the color tone imparted by the oxidation dye is not so vivid or that the color of the hair dyed with the nitro dye, which is ordinarily employed as a direct dye and produces a vivid-color, markedly fades over time and becomes dull quickly although the color tone immediately after dyeing is very vivid. A variety of direct dyes such as cationic direct dyes and nitro dyes have been used in combination in permanent hair dye products in order to produce a vivid color.

Direct dyes available at present however cannot bring about sufficient effects. Moreover, the number of direct dyes that can be used in combination with an oxidation dye is limited because they are required to have stability against alkali peroxides during the hair dying process. In any case, the color fades very quickly due to the loss of the direct dye as a result of washing or exposure to light. This phenomenon is marked in damaged or porous hair (hair having pores formed therein).

The present inventors provided azo dyes having a dissociative proton as a direct dye capable of overcoming the above-described problems (for example, refer to Patent Documents 1 and 2). These dyes however still have problems to be improved, such as resistance to light, shampooing, sweat, friction or heat, or stability against an alkalizing agent or an oxidizing agent.

[Patent Document 1] JP-A-2003-342139

[Patent Document 2] JP-A-2004-107343

DISCLOSURE OF THE INVENTION

In the present invention, there is provided a hair dye composition comprising an azo dye represented by the following formula (1):

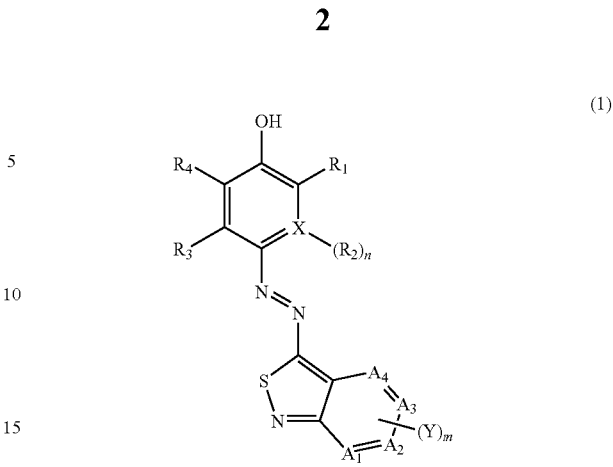

(wherein, $R_1$, $R_2$, $R_3$, and $R_4$ each independently represents a hydrogen atom, aliphatic hydrocarbon group, aryl group, halogen atom, acyl group, cyano group, acylamino group, aliphatic oxycarbonyl group, aryloxycarbonyl group, carbamoyl group, aliphatic sulfonyl group, arylsulfonyl group, sulfamoyl group, aliphatic oxycarbonylamino group, aryloxycarbonylamino group, sulfo group, carboxy group, carbamoylamino group, sulfamoylamino group or aliphatic or aromatic sulfonylamino group, wherein $R_1$ and $R_2$, and/or $R_3$ and $R_4$ may be coupled to form a 5- or 6-membered aromatic or non-aromatic ring; X represents a carbon atom or nitrogen atom, with the proviso that when X represents a carbon atom, n stands for 1 and when X represents a nitrogen atom, n stands for 0; $A_1$, $A_2$, $A_3$ and $A_4$ each independently represents a nitrogen atom or represents a carbon atom substituted by Y or having a hydrogen atom, with the proviso that at least one of $A_1$, $A_2$, $A_3$ and $A_4$ is a nitrogen atom; and Y represents a substituent with the proviso that m stands for an integer from 0 to 3), or a salt thereof.

MODE FOR CARRYING OUT THE INVENTION

The present invention relates to a hair dye composition capable of strongly imparting a vivid color to hair without causing decomposition of the dye, having excellent resistance to light, shampooing, sweat, friction and heat, being stable against an alkalizing agent and oxidizing agent, having a strong dyeing power, and having less color fading over time.

The present inventors have found that a hair dye composition containing an azo dye represented by the formula (1) (which will hereinafter be called "azo dye (1)") can strongly impart the hair with a vivid color selected from wide range of colors without causing decomposition of the dye during hair dyeing and exhibits excellent resistance to light, shampooing, sweat, friction and heat.

(Azo Dye (1))

The azo dye (1) to be used in the present invention embraces not only tautomers in the non-dissociation state as shown below by the reaction scheme but also each isomer in the dissociation state. The tautomers embrace not only an azo-hydrazo tautomer represented by the following formula (1)' but also a tautomer via an Ar moiety as shown, for example, by the following formula (1)". The azo dye (1) dissociates a proton under use conditions, undergoes a change in hue, and thereby gives a desired color to hair.

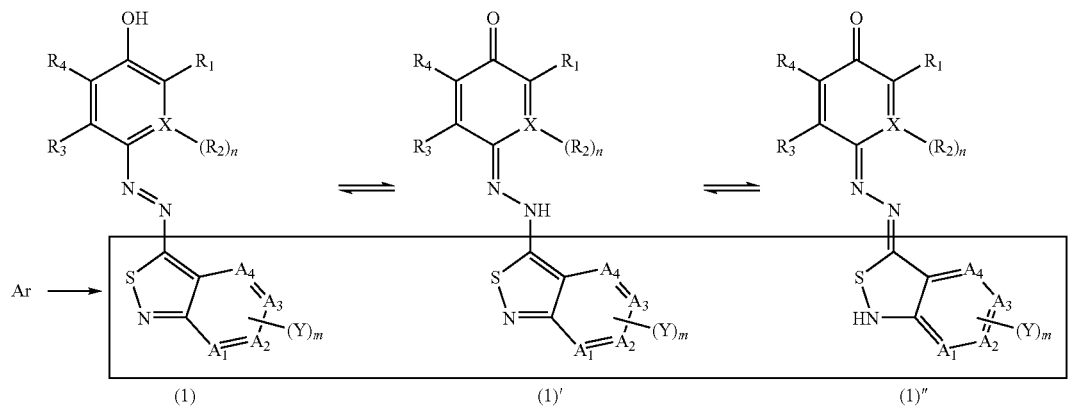

As $R_1$ to $R_4$ in the formula (1), the aliphatic hydrocarbon group is preferably an optionally-substituted, saturated or unsaturated group having from 1 to 15 carbon atoms in total, and for example, includes methyl, ethyl, vinyl, allyl, ethynyl, isopropenyl and 2-ethylhexyl. The aryl group is preferably an optionally-substituted group having from 6 to 16 carbon atoms in total, and for example, includes phenyl, 4-nitrophenyl, 2-nitrophenyl, 2-chlorophenyl, 2,4-dichlorophenyl, 2,4-diemethylphenyl, 2-methylphenyl, 4-methoxyphenyl, 2-methoxyphenyl and 2-methoxycarbonyl-4-nitrophenyl. Examples of the halogen atom include fluorine, chlorine, bromine and iodine. The acyl group is preferably an aromatic or aliphatic acyl group having from 2 to 15 carbon atoms in total, and for example, includes acetyl, pivaloyl and benzoyl. The acylamino group is preferably an optionally-substituted group having from 1 to 8 carbon atoms in total, and for example, includes acetylamino, propionylamino and chloroacetylamino. The aliphatic oxycarbonyl group is preferably an optionally-substituted, saturated or unsaturated group having from 1 to 16 carbon atoms in total, and for example, includes methoxycarbonyl and butoxycarbonyl. The aryloxycarbonyl group is preferably an optionally-substituted group having from 7 to 17 carbon atoms in total, and for example, includes phenoxycarbonyl. The carbamoyl group is preferably an optionally-substituted group having from 1 to 12 carbon atoms in total, and for example, includes carbamoyl and dimethylcarbamoyl. The aliphatic sulfonyl group is preferably an optionally-substituted, saturated or unsaturated group having from 1 to 15 carbon atoms in total, and for example, includes methanesulfonyl, butanesulfonyl and methoxyethanesulfonyl. The arylsulfonyl group is preferably an optionally-substituted group having from 6 to 16 carbon atoms in total, and for example, includes phenylsulfonyl, 4-t-butylphenylsulfonyl, 4-toluenesulfonyl and 2-toluenesulfonyl. The sulfamoyl group is preferably an optionally-substituted group having from 0 to 12 carbon atoms in total, and for example, includes sulfamoyl and dimethylsulfamoyl. The aliphatic oxycarbonylamino group is preferably an optionally-substituted group having from 1 to 6 carbon atoms in total, and for example, includes methoxycarbonylamino, ethoxycarbonylamino and methoxyethoxycarbonylamino. The aryloxycarbonylamino group is preferably an optionally-substituted group having from 1 to 10 carbon atoms in total, and for example, includes phenoxycarbonylamino and p-chlorophenoxycarbonylamino. The carbamoylamino group is preferably an optionally-substituted group having from 1 to 8 carbon atoms in total, and for example, includes monomethylaminocarbonylamino, dimethylaminocarbonylamino, bis-(2-methoxyethyl)aminocarbonylamino, monoethylaminocarbonylamino, diethylaminocarbonylamino, and N-phenyl-N-methylaminocarbonylamino. The sulfamoylamino group is preferably an optionally-substituted group having from 1 to 8 carbon atoms in total, and for example, includes sulfamoylamino, N-ethylsulfamoylamino, N,N-dimethylsulfamoylamino and N,N-diethylsulfamoylamino. The aliphatic or aromatic sulfonylamino group is preferably an optionally-substituted group having from 1 to 18 carbon atoms in total, and for example, includes methanesulfonylamino, ethanesulfonylamino, chloromethanesulfonylamino, propanesulfonylamino, butanesulfonylamino, n-octanesulfonylamino, n-dodecanesulfonylamino, benzenesulfonylamino, 3-mesylaminobenzenesulfonylamino, and 4-methylbenzenesulfonylamino. Examples of the 5- or 6-membered aromatic or non-aromatic ring formed by coupling of $R_1$ and $R_2$, and/or $R_3$ and $R_4$ include benzene ring and lactam ring.

Of these, preferred as $R_1$ are halogen atoms, cyano group, acylamino groups, carbamoyl groups, sulfamoyl groups, aliphatic oxycarbonylamino groups, carbamoylamino groups, sulfamoylamino groups, and aliphatic or aromatic sulfonylamino groups, of which halogen atoms, cyano group, acylamino groups and carbamoyl groups are more preferred, halogen atoms and acylamino groups are even more preferred, and chlorine and fluorine atoms are even more preferred.

Preferred as $R_2$ are hydrogen atom, halogen atoms and aliphatic hydrocarbon groups, of which hydrogen atom and halogen atoms are more preferred, with hydrogen atom being even more preferred.

As $R_3$, preferred are hydrogen atom, halogen atoms, acylamino groups, aliphatic oxycarbonylamino groups, carbamoylamino groups, sulfamoylamino groups, and aliphatic or aromatic sulfonylamino groups, of which hydrogen atom, halogen atoms and acylamino groups are more preferred, with hydrogen atom being even more preferred.

As $R_4$, preferred are hydrogen atom, halogen atoms and acylamino groups, of which hydrogen atom and acylamino groups are more preferred, with hydrogen atom being even more preferred. It is also preferred that $R_3$ and $R_4$ are coupled to form a benzene or lactam ring.

X is preferably a carbon atom.

Examples of Y include hydrogen atom and substituents similar to those exemplified for $R_1$ to $R_4$. Of these, halogen atoms, alkyl groups, cyano group, alkoxy groups, alkylthio groups, alkyl- and arylsulfonylamino groups, sulfamoyl groups, alkylsulfonyl groups, arylsulfonyl groups, acyl groups, alkoxycarbonyl groups, and carbamoyl groups are preferred, with halogen atoms, cyano group and alkylthio groups being more preferred and cyano group and alkylthio groups being even more preferred.

Specific examples of the azo dye (1) to be used in the present invention are shown by the following formulas (D-1) to (D-56).

(D-1)
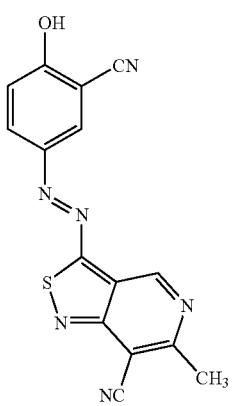

(D-2)
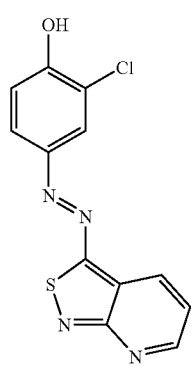

(D-3)
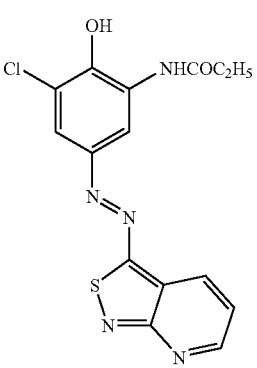

-continued (D-4)
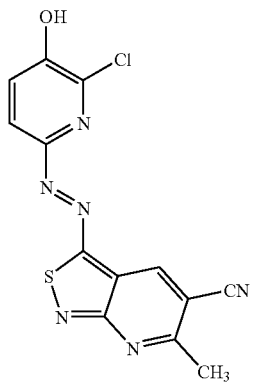

(D-5)
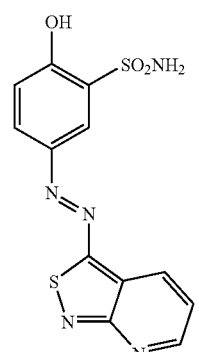

(D-6)
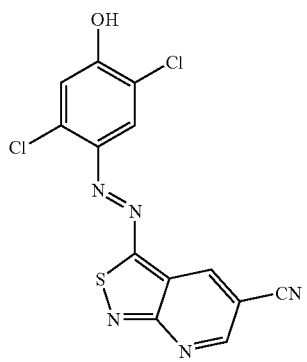

(D-7)
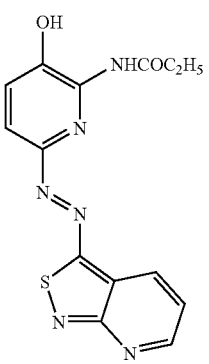

-continued
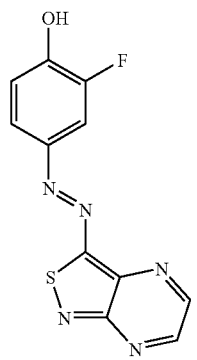
(D-8)
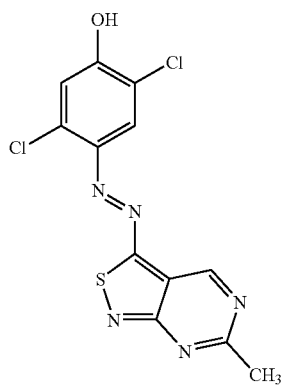
(D-12)
(D-9)
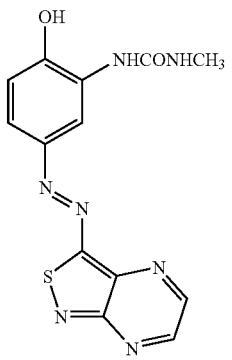
(D-13)
(D-10)
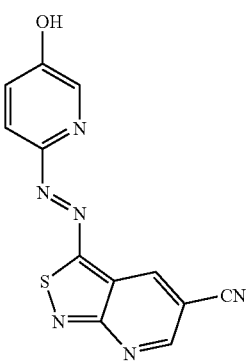
(D-14)
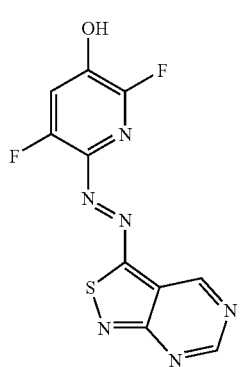
(D-11)
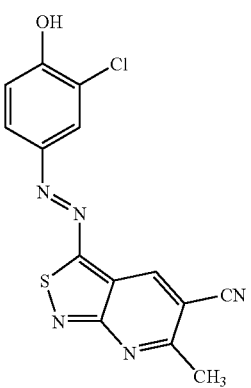
(D-15)

-continued
(D-16)
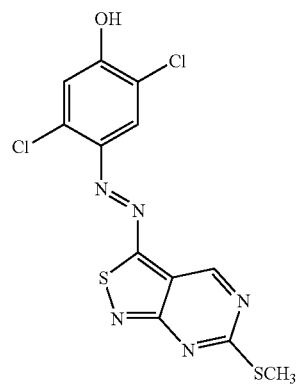
(D-17)
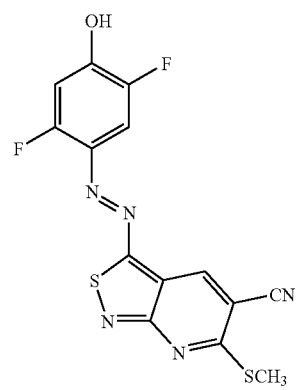
(D-18)
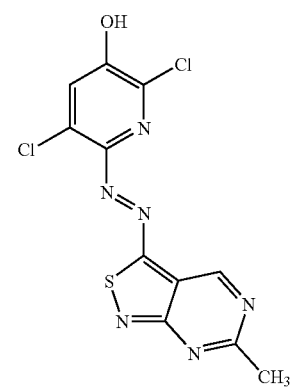
(D-19)
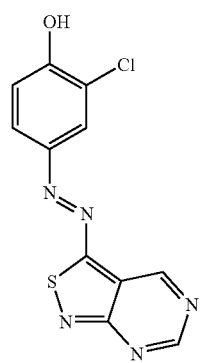
-continued
(D-20)
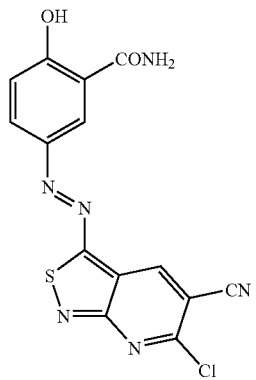
(D-21)
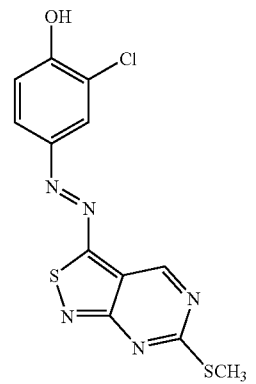
(D-22)
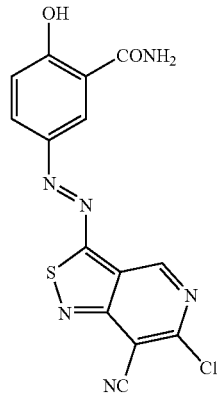
(D-23)
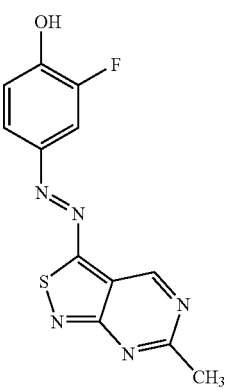

(D-24)
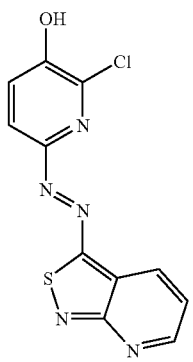
(D-25)
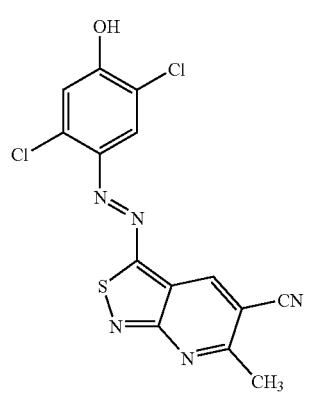
(D-26)
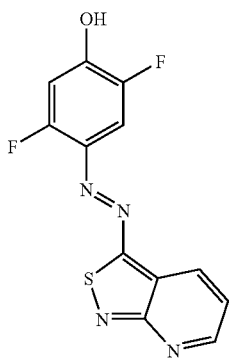
(D-27)
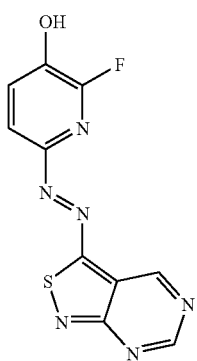
(D-28)
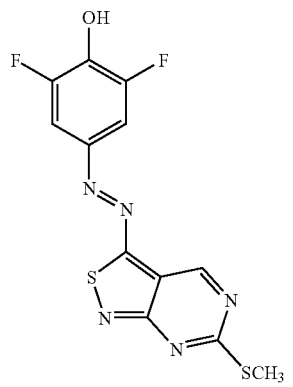
(D-29)
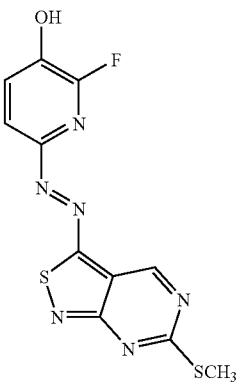
(D-30)
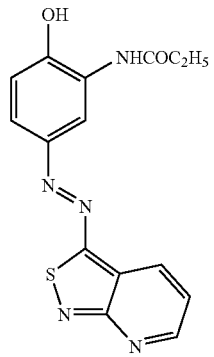
(D-31)
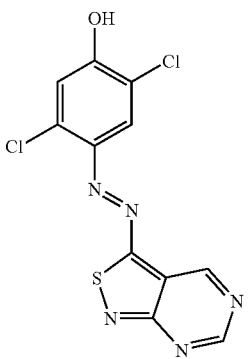

-continued
(D-32) 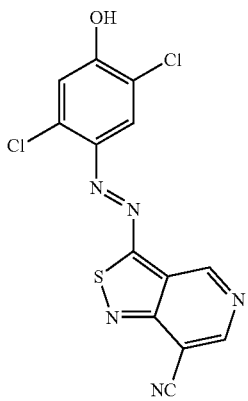
(D-33) 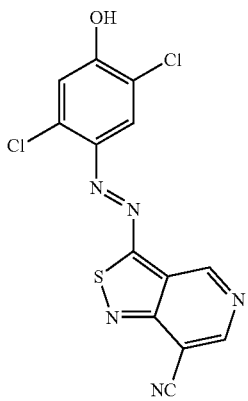
(D-34) 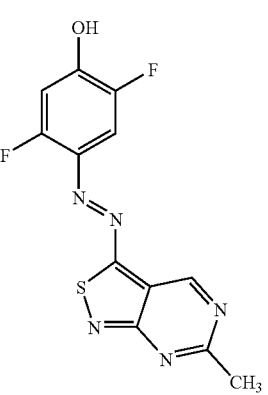
(D-35) 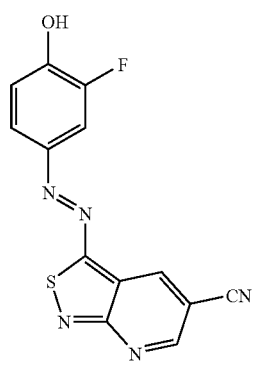
-continued
(D-36) 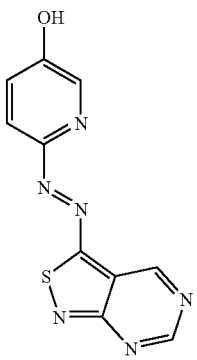
(D-37) 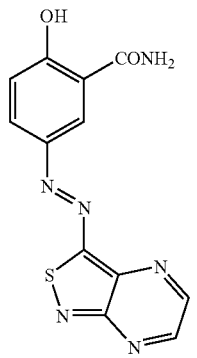
(D-38) 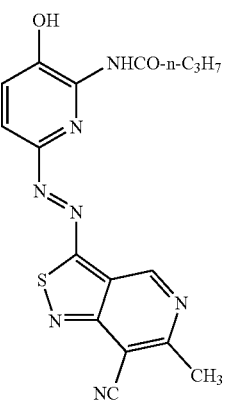
(D-39) 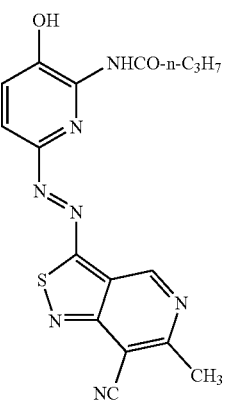

-continued
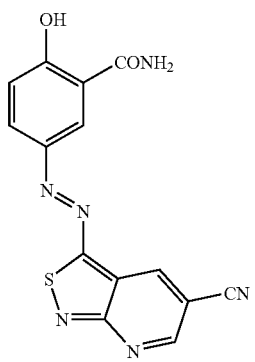 (D-40)
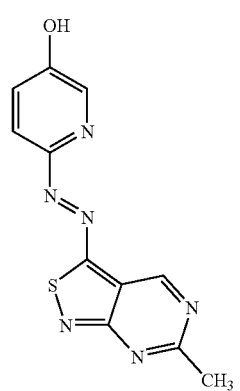 (D-41)
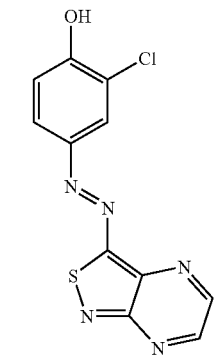 (D-42)
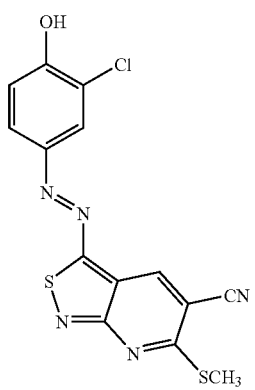 (D-43)
-continued
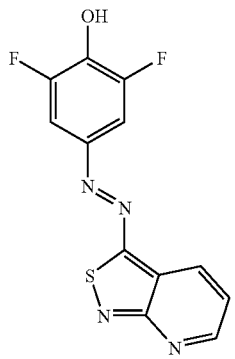 (D-44)
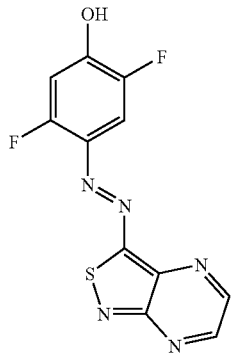 (D-45)
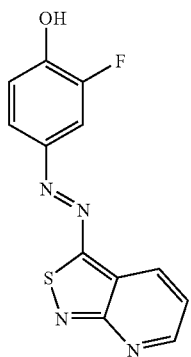 (D-46)
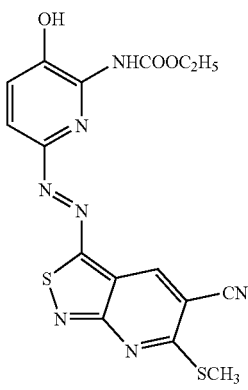 (D-47)

-continued
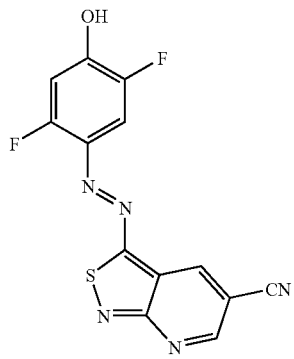
(D-48)
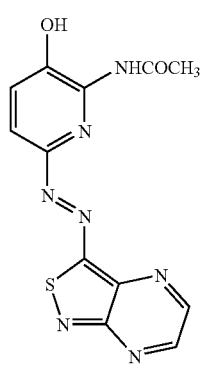
(D-49)
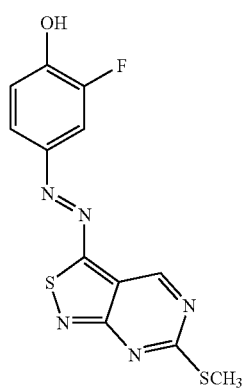
(D-50)
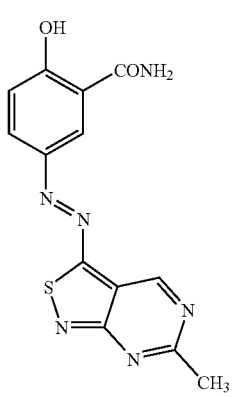
(D-51)
-continued
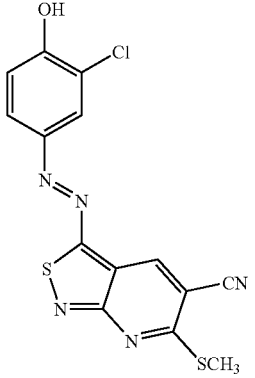
(D-52)
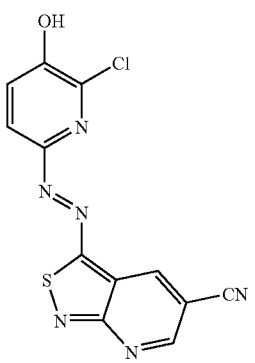
(D-53)
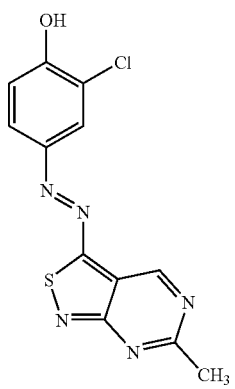
(D-54)
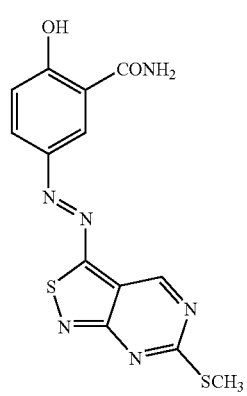
(D-55)

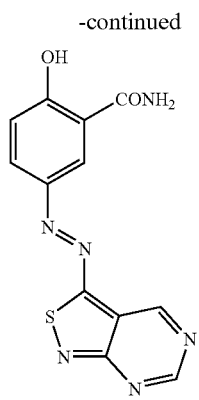

(D-56)

The azo dye (1) may be a salt of an inorganic or organic acid or an inorganic or organic alkali. Examples of the inorganic or organic acid include hydrochloric acid, sulfuric acid, phosphoric acid, acetic acid, propionic acid, lactic acid and citric acid. Examples of the inorganic or organic alkali include ammonium hydroxide, sodium hydroxide, potassium hydroxide and 2-ethanolammonium hydroxide.

The azo dye (1) can be synthesized, for example, by diazotizing the following amino compound (A) serving as a diazo component and then coupling it with a phenol coupler or hydroxypyridine coupler in accordance with any procedures disclosed in JP-A-2003-342139, JP-A-2000-248188, or the like.

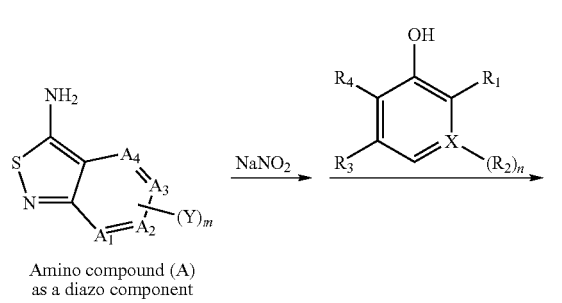

Amino compound (A) as a diazo component

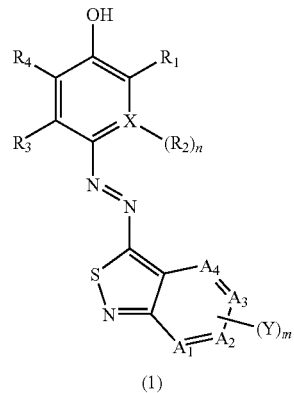

(1)

The content of the azo dye (1) in the whole composition (after mixing all the components when the composition is a two part or three part composition, which will be applied equally hereinafter) is preferably from to 20 wt. %, more preferably from 0.001 to 20 wt. %, even more preferably from 0.05 to 10 wt. %, even more preferably from 0.1 to 5 wt. %.

Since the azo dye (1) has excellent storage stability within a wide pH range from 2 to 11 within which ordinary hair dyes have been used, the hair dye composition of the present invention can be used at any pH within the above-described range, of which a range of pH 5 or greater is preferred from the viewpoint of the dyeing property. The hair dye composition of the present invention can be used at pH 8 or greater, moreover at pH 8 to 11 at which it has a high dyeing property since the azo dye (1) is highly stable against alkalizing agents. Thus, without decomposition of a direct dye even after long storage, the hair dye composition of the present invention can maintain its high dyeing power.

[Another Dye]

It is possible to add another direct dye or oxidation dye to the hair dye composition of the present invention to change the color tone thereof.

As another direct dye, known direct dyes such as basic dye, cationic dye, nitro dye and disperse dye can be added. Specific examples include Basic Blue 7 (C.I. 42595), Basic Blue 26 (C.I. 44045), Basic Blue 99 (C.I. 56059), Basic Violet 10 (C.I. 45170), Basic Violet 14 (C.I. 42515), Basic Brown 16 (C.I. 12250), Basic Brown 17 (C.I. 12251), Basic Red 2 (C.I. 50240), Basic Red 12 (C.I. 48070), Basic Red 22 (C.I. 11055), Basic Red 46 (C.I. 110825), Basic Red 76 (C.I. 12245), Basic Red 118 (C.I. 12251:1), Basic Yellow 28 (C.I. 48054) and Basic Yellow 57 (C.I. 12719); cationic dyes described in JP-A-58-2204, JP-A-9-118832, JP-A-8-501322 and JP-A-8-507545; and methine type cationic dyes having a cyanine structure represented by the following formulas:

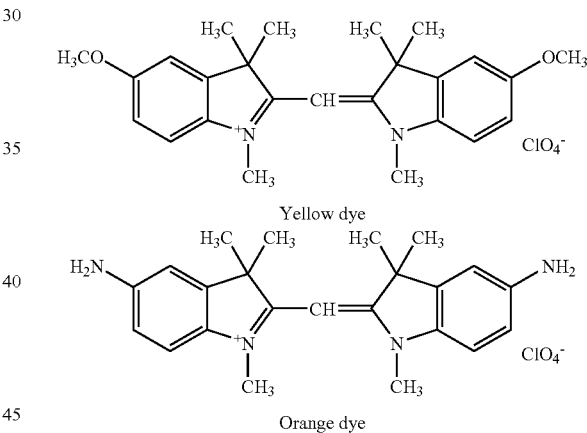

Yellow dye

Orange dye

Direct dyes described in, for example, JP-A-2002-275040, JP-A-2003-107222, JP-A-2003-107223, JP-A-2003-113055, JP-A-2004-107343, JP-A-2003-342139 and JP-A-2004-155746 can also be added.

In the hair dye composition of the present invention, an oxidation dye can be used in combination with the azo dye (1). Such a combined use enables markedly vivid and intense dyeing that cannot be accomplished by the single use of an oxidation dye. As the oxidation dye, known developers and couplers ordinarily employed for oxidation type hair dyes can be used.

Examples of the developer include para-phenylenediamine, toluene-2,5-diamine, 2-chloro-para-phenylenediamine, N-methoxyethyl-para-phenylenediamine, N,N-bis(2-hydroxyethyl)-para-phenylenediamine, 2-(2-hydroxyethyl)-para-phenylenediamine, 2,6-dimethyl-para-phenylenediamine, 4,4'-diaminodiphenylamine, 1,3-bis(N-(2-hydroxyethyl)-N-(4-aminophenyl)amino)-2-propanol, PEG-3,2,2'-para-phenylenediamine, para-aminophenol, para-methylaminophenol, 3-methyl-4-aminophenol, 2-aminomethyl-4-aminophenol, 2-(2-hydroxyethylaminomethyl)-4-aminophenol, ortho-aminophenol, 2-amino-5-methylphenol, 2-amino-6-methylphenol, 2-amino-5-acetamidophenol, 3,4-diaminobenzoic acid, 5-aminosalicylic acid, 2,4,5,6-tetraminopyrimidine, 2,5,6-triamino-4-hydroxypyrimidine and 4,5-diamino-1-(4'-chlorobenzyl)pyrazole, and salts thereof.

Examples of the coupler include meta-phenylenediamine, 2,4-diaminophenoxyethanol, 2-amino-4-(2-hydroxyethylamino)anisole, 2,4-diamino-5-methylphenetole, 2,4-diamino-5-(2-hydroxyethoxy)toluene, 2,4-dimethoxy-1,3-diaminobenzene, 2,6-bis(2-hydroxyethylamino)toluene, 2,4-diamino-5-fluorotoluene, 1,3-bis(2,4-diaminophenoxy)propane, meta-aminophenol, 2-methyl-5-aminophenol, 2-methyl-5-(2-hydroxyethylamino)phenol, 2,4-dichloro-3-aminophenol, 2-chloro-3-amino-6-methylphenol, 2-methyl-4-chloro-5-aminophenol, N-cyclopentyl-meta-aminophenol, 2-methyl-4-methoxy-5-(2-hydroxyethylamino)phenol, 2-methyl-4-fluoro-5-aminophenol, resorcin, 2-methylresorcin, 4-chlororesorcin, 1-naphthol, 1,5-dihydroxynaphthalene, 1,7-dihydroxynaphthalene, 2,7-dihydroxynaphthalene, 2-isopropyl-5-methylphenol, 4-hydroxyindole, 5-hydroxyindole, 6-hydroxyindole, 7-hydroxyindole, 6-hydroxybenzomorpholine, 3,4-methylenedioxyphenol, 2-bromo-4,5-methylenedioxyphenol, 3,4-methylenedioxyaniline, 1-(2-hydroxyethyl)amino-3,4-methylenedioxybenzene, 2,6-dihydroxy-3,4-dimethylpyridine, 2,6-dimethoxy-3,5-diaminopyridine, 2,3-diamino-6-methoxypyridine, 2-methylamino-3-amino-6-methoxypyridine, 2-amino-3-hydroxypyridine and 2,6-diaminopyridine, and salts thereof.

As each of the developer and coupler, two or more of the above-described ones may be used in combination. The total content of the developer and coupler in the whole composition is preferably from 0.0005 to 20 wt. %, more preferably from 0.01 to 19 wt. %, even more preferably from 0.01 to 15 wt. %, even more preferably from 0.5 to 10 wt. %.

To the hair dye composition of the present invention, an autoxidation dye typified by indoles, indolines or the like can be added further.

The total content of the azo dye (1), another direct dye and oxidation dye in the whole hair dye composition of the present invention is preferably from 0.001 to 20 wt. %, more preferably from 0.01 to 20 wt. %, even more preferably from 0.5 to 15 wt. %.

[Other Components]

Examples of the alkali agent to be used in the hair dye composition of the present invention include ammonia; alkanolamines such as monoethanolamine and isopropanolamine and salts thereof; guanidium salts such as guanidine carbonate; and hydroxides such as sodium hydroxide. The content of the alkali agent in the whole composition is preferably from 0.01 to 20 wt. %, more preferably from 0.1 to 10 wt. %, even more preferably from 0.5 to 5 wt. %.

Since the azo dye (1) to be used in the present invention has high stability against an oxidizing agent, it can be applied to the hair after mixing with an oxidizing agent. In other words, it can be provided in the form of a two part hair dye composed of a first part containing the azo dye (1) (which may contain any known direct dye or oxidation dye) and a second part containing an oxidizing agent. In this case, hair dyeing and bleaching can be performed simultaneously, to achieve more vivid hair dyeing.

Examples of the oxidizing agent include hydrogen peroxide; persulfates such as ammonium persulfate, potassium persulfate and sodium persulfate; perborates such as sodium perborate; percarbonates such as sodium percarbonate; and bromates such as sodium bromate and potassium bromate. Of these, hydrogen peroxide is preferred from the viewpoints of its good hair bleaching properties, and stability and effectiveness of the azo dye (1). It is also preferred to use hydrogen peroxide in combination with another oxidizing agent as an oxidizing aid. Use of hydrogen peroxide in combination with a persulfate is especially preferred. The content of the oxidizing agent in the whole composition is preferably from 0.5 to 30 wt. %, more preferably from about 1 to 20 wt. %. When hydrogen peroxide and a persulfate are used in combination, it is preferred that the content of hydrogen peroxide is from 0.5 to 10 wt. %, that of the persulfate is from 0.5 to 25 wt. %, and the total content of them is from 1 to 30 wt. %, each based on the whole composition.

A mixing ratio of the first part containing the azo dye (1) with the second part containing the oxidizing agent preferably ranges from about 2:1 to 1:3 in terms of a volume ratio.

It is also possible to add, to a known two-part oxidation type hair dye or bleaching agent composed of a first part containing an alkali agent (that may contain any other known direct dye) and a second part containing an oxidizing agent; or a known three-part oxidation type hair dye or bleaching agent composed of a first part containing an alkali agent (that may contain any other known direct dye), second part containing an oxidizing agent and a third part containing an oxidizing aid; before or during use thereof, a one-part hair dye composition containing the azo dye (1) in combination, in order to change the color tone of the oxidation type hair dye.

The azo dye (1) can have improved dyeing property and color shampoo fastness by incorporating therein an organic solvent that readily penetrates into the hair and is selected from aromatic alcohols, lower alkylene carbonates, N-alkylpyrrolidones and formamides. Examples of the aromatic alcohols include benzyl alcohol, phenethyl alcohol, γ-phenylpropyl alcohol, cinnamic alcohol, anis alcohol, p-methylbenzyl alcohol, α,α-dimethylphenethyl alcohol, α-phenylethanol and phenoxyethanol; those of the lower alkylene carbonates include carbonates having a $C_{2-6}$ alkylene group such as ethylene carbonate, propylene carbonate and butylene carbonate; those of the N-alkylpyrrolidones include N-methylpyrrolidone and N-ethylpyrrolidone; and those of the formamides include N-cyclohexylformamide, N,N-dimethylformamide and N-methylformamide. From the viewpoints of dyeing property and color shampoo fastness, benzyl alcohol, benzyloxyethanol, propylene carbonate and the like are preferred. Such organic solvents may be used in combination of two or more. The content of the organic solvent in the whole composition is preferably from 1 to 50 wt. %, more preferably from 5 to 45 wt. % from the viewpoints of dyeing property and color shampoo fastness.

Addition of a polyol, polyol alkyl ether, cationic polymer, amphoteric polymer, or silicone to the hair dye composition of the present invention is preferred, because it is effective for imparting uniform dye affinity and improved hair cosmetic effects thereto.

In addition to the above-described components, other components ordinarily employed as cosmetic raw materials can be incorporated in the hair dye composition of the present invention. Examples of such optional components include hydrocarbons, animal or plant oils or fats, higher fatty acids, penetration promoters, cationic surfactants, natural or synthetic polymers, higher alcohols, ethers, amphoteric surfactants, nonionic surfactants, anionic surfactants, protein derivatives, amino acids, preservatives, chelating agents, stabilizers, antioxidants, plant extracts, crude drug extracts, vitamins, colorants, perfumes, and ultraviolet absorbers.

The hair dye composition of the present invention can be prepared in a conventional manner into a one-part composition, a two-part composition composed of a first part containing an alkali agent and a second part containing an oxidizing agent, or a three-part composition composed of these two parts and a powdery oxidizing agent such as persulfate. The azo dye (1) may be incorporated in either one or both of these parts of the two-part or three-part composition. When the hair dye composition of the present invention is a one-part type, it is applied to the hair directly. When it is a two- or three-part type, a mixture of the components is applied to the hair upon hair dyeing. Alternatively, the one-part composition containing the direct dye (1) may be mixed with the two-part or three-part composition during mixing their components, followed by application to the hair.

The hair dye composition can be provided in the product form of powder, transparent liquid, emulsion, cream, gel, paste, aerosol, aerosol foam, or the like. The viscosity of the composition when it is applied to the hair (after mixing all the components in case of a two-part or three-part composition) is preferably from 1,000 to 100,000 mPa·s, more preferably from 5,000 to 50,000 mPa·s, even more preferably from 10,000 to 40,000 mPa·s (Brookfield rotary viscometer, No. 5 spindle, 5 rpm, at 20° C.).

The hair dye composition of the present invention is usable for dyeing the human or animal hair. The dyeing method includes applying the hair dye composition to the hair, shampooing the hair after completion of the dyeing, and drying the shampooed hair.

EXAMPLES

Synthesis Example 1

Exemplary Compound (D-2) was synthesized by the following method.

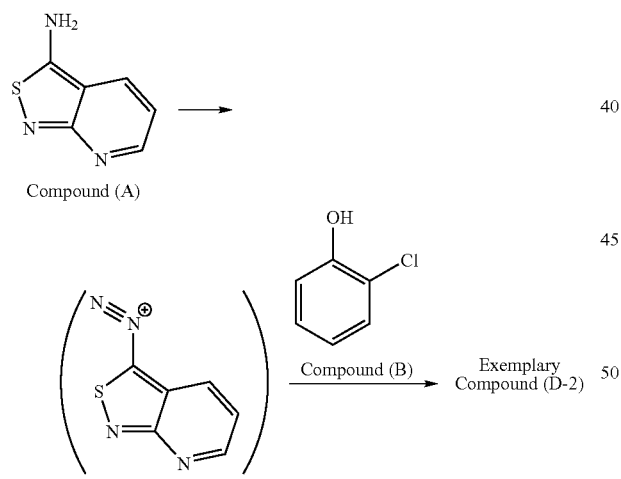

Compound (A) (15.1 g, 0.1 mole) was suspended in 300 mL of phosphoric acid. To the resulting suspension was added 8.3 g (0.12 mole) of sodium nitrite by portions while maintaining the internal temperature at 5° C. or less and the reaction mixture was stirred for 30 minutes. A solution obtained separately by dissolving 12.9 g (0.1 mole) of Compound (B) in 100 mL of acetic acid was added to the reaction mixture, followed by stirring at 10° C. for 5 hours. Water (2 liters) was then added and the resulting mixture was stirred for 1 hour. Crystals thus precipitated were collected by filtration and washed sufficiently with water. The crystals thus obtained were dried, and purified using silica gel column chromatography. After crystallization from 400 mL of a 1:1 (mixing ratio in mL) methanol:water mixture and filtration, the crystals were washed with 100 mL of the mixed solvent and dried, whereby 8.7 g of Exemplary compound (D-2) was obtained as black crystals (yield: 29.9%).

The diazo component (Compound (A)) used in the above reaction can be synthesized with Compound (F) as a starting substance in accordance with the process described in JP-A-56-55455.

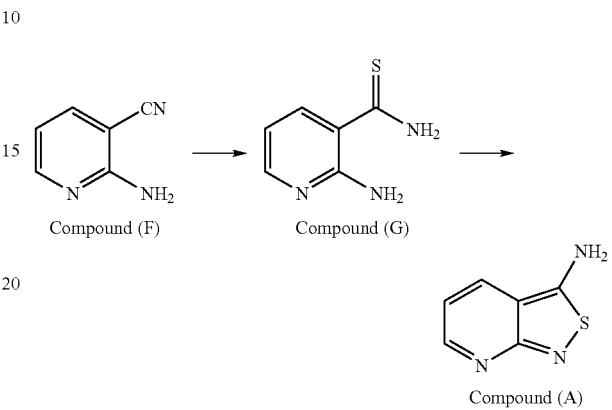

Synthesis Example 2

Exemplary compound (D-3) was synthesized by the following method.

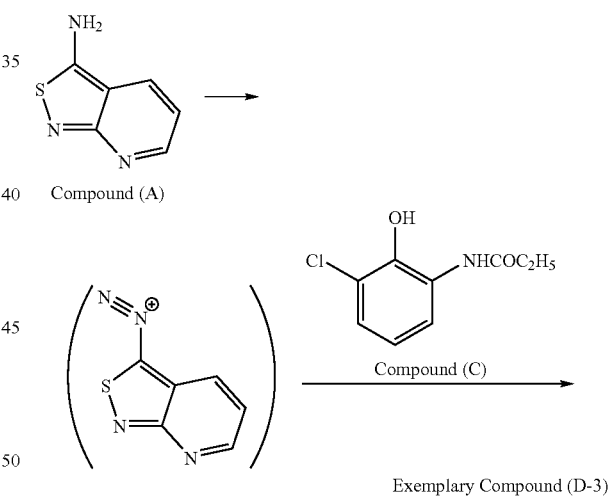

Compound (A) (15.1 g, 0.1 mole) was suspended in 300 mL of phosphoric acid. To the resulting suspension was added 8.3 g (0.12 mole) of sodium nitrite by portions while maintaining the internal temperature at 5° C. or less and the reaction mixture was stirred for 30 minutes. A solution obtained separately by dissolving 20 g (0.1 mole) of Compound (C) in 150 mL of acetic acid was added to the reaction mixture, followed by stirring at 10° C. for 5 hours. Water (2 liters) was then added and the resulting mixture was stirred for 1 hour. Crystals thus precipitated were collected by filtration and washed sufficiently with water. The crystals thus obtained were dried, and purified using silica gel column chromatography. After crystallization from 400 mL of methanol and filtration, the crystals were washed with 100 mL of methanol and dried, whereby 12 g of Exemplary compound (D-3) was obtained as black crystals (yield: 33.1%).

The coupler component (Compound (C)) used in the above-described reaction can be synthesized from Compound (H) as a starting substance, by replacing the chlorine atom thereof with a hydroxy group (Compound (I)), and performing reduction and amidation.

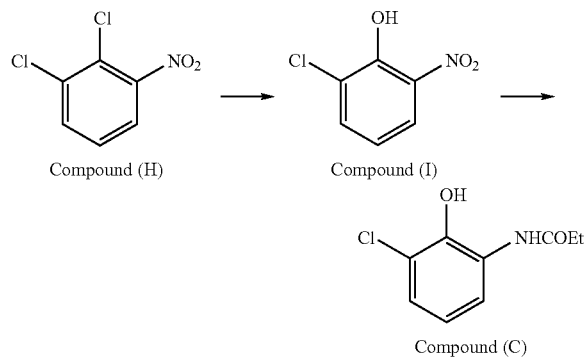

Synthesis 3

Exemplary compound (D-7) was synthesized by the following method.

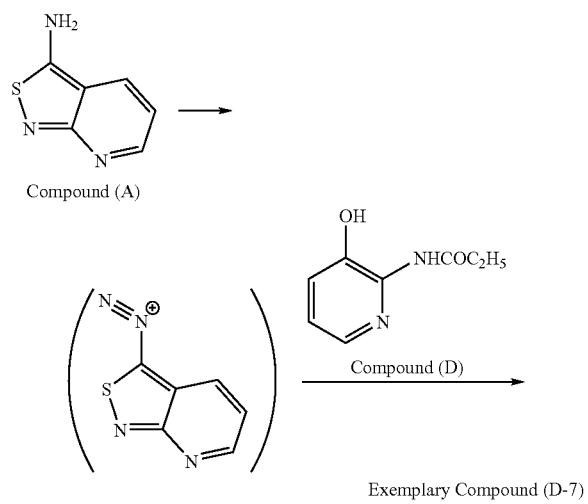

Compound (A) (15.1 g, 0.1 mole) was dissolved in 160 mL of phosphoric acid. A solution of 16.6 g (0.1 mole) of Compound (D) in 60 mL of acetic acid was then added to the resulting solution. Under ice cooling, 6.9 g (0.1 mole) of sodium nitrite was added by portions while maintaining the internal temperature at 5° C. or less, and the reaction mixture was stirred for 120 minutes. Water (2 liters) was then added and the resulting mixture was stirred for 1 hour. Crystals thus precipitated were collected by filtration and washed sufficiently with water. The crystals thus obtained were dried, and purified using silica gel column chromatography. After crystallization from 100 mL of methanol and filtration, the crystals were washed with 50 mL of methanol cooled to 10° C. or less and dried, whereby 9.6 g of Exemplary compound (D-9) was obtained as reddish brown crystals (yield: 29.3%).

The coupler component (Compound (D)) used in the above-described reaction can be synthesized from Compound (J) as a starting substance, by amidation.

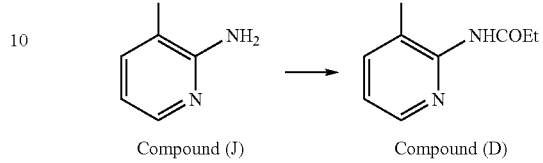

Synthesis Example 4

Exemplary compound (D-26) was synthesized by the following method.

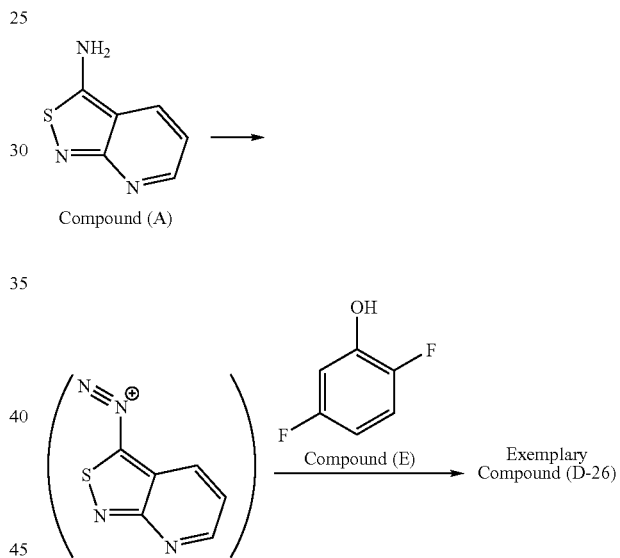

Compound (A) (15.1 g, 0.1 mole) was dissolved in 160 mL of phosphoric acid. A solution of 13 g (0.1 mole) of Compound (E) in 45 mL of acetic acid was then added. Under ice cooling, 6.9 g (0.1 mole) of sodium nitrite was added by portions to the resulting solution while maintaining the internal temperature at 5° C. or less, and the reaction mixture was stirred for 120 minutes. Water (2 liters) was then added and the resulting mixture was stirred for 1 hour. Crystals thus precipitated were collected by filtration and washed sufficiently with water. The crystals thus obtained were dried, and purified using silica gel column chromatography. After crystallization from 100 mL of methanol and filtration, the crystals were washed with 50 mL of methanol cooled to 10° C. or less and dried, whereby 10 g of Exemplary compound (D-26) was obtained as reddish brown crystals (yield: 34.2%).

Synthesis Example 5

Exemplary compound (D-20) was synthesized by the following method.

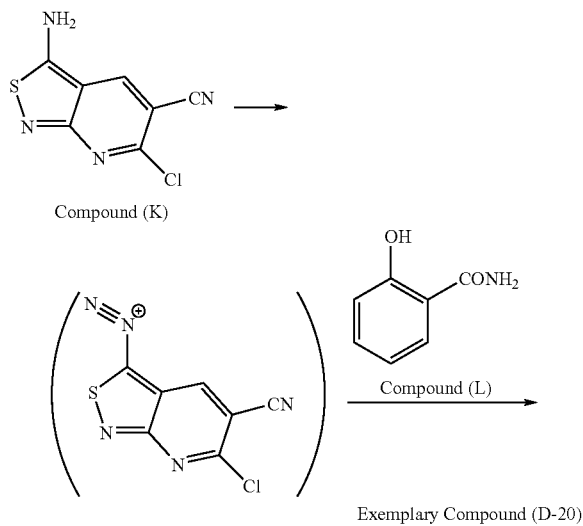

Compound (K)

Exemplary Compound (D-20)

method as described in JP-A-56-55455 by using Compound (M) as a starting substance.

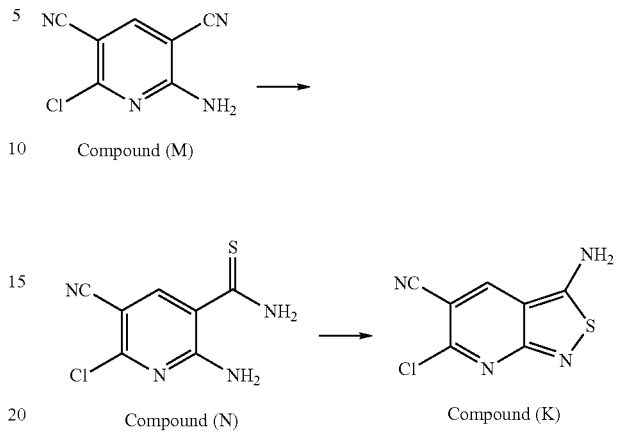

Compound (K) (21 g, 0.1 mole) was dissolved in 200 mL of phosphoric acid. A solution of 13.7 g (0.1 mole) of Compound (L) in 50 mL of acetic acid was then added. Under ice cooling, 6.9 g (0.1 mole) of sodium nitrite was added by portions to the resulting mixture while maintaining the internal temperature at 5° C. or less, and the reaction mixture was stirred for 120 minutes. Water (2 liters) was then added and the resulting mixture was stirred for 1 hour. Crystals thus precipitated were collected by filtration and washed sufficiently with water. The crystals thus obtained were dried, and purified using silica gel column chromatography. After crystallization from 100 mL of methanol and filtration, the crystals were washed with 50 mL of methanol cooled to 10° C. or less and dried, whereby 10.1 g of Exemplary compound (D-20) was obtained as reddish brown crystals (yield: 28.1%).

The diazo component (Compound (K)) used for the above-described reaction can be synthesized in accordance with the method as described in JP-A-56-55455 by using Compound (M) as a starting substance.

Examples 1 to 6

One-part hair dyes shown in Table 1 were prepared in a conventional manner.

TABLE 1

| (w.t %) | Examples | | | | | |
| --- | --- | --- | --- | --- | --- | --- |
|  | 1 | 2 | 3 | 4 | 5 | 6 |
| Azo dye (D-2) | 0.2 | — | 0.1 | 0.1 | 0.1 | — |
| Azo dye (D-3) | — | 0.2 | — | 0.2 | — | — |
| Azo dye (D-7) | — | 0.2 | — | 0.2 | — | — |
| Azo dye (D-15) | — | — | 0.1 | — | 0.1 | — |
| Azo dye (D-26) | 0.1 | — | — | — | — | 0.1 |
| HC Red 3 | — | — | 0.2 | 0.2 | 0.2 | 0.2 |
| Basic Blue 99 | — | — | — | — | 0.1 | 0.1 |
| Ammonia (28 wt. %) | 8.0 | 8.0 | 8.0 | 8.0 | 8.0 | 8.0 |
| Isopropyl alcohol | 1.5 | 1.5 | 1.5 | 1.5 | 1.5 | 1.5 |
| Ethanol | 6.0 | 6.0 | 6.0 | 6.0 | 6.0 | 6.0 |
| Benzyl alcohol | 8.0 | 8.0 | 8.0 | 8.0 | 8.0 | 8.0 |
| PEG-12 | — | — | — | — | — | — |
| Ammonium chloride [*1] | q.s. | q.s. | q.s. | q.s. | q.s. | q.s. |
| Hydroxypropyl xanthan gum | 2.0 | 2.0 | 2.0 | 2.0 | 2.0 | 2.0 |
| Polyether-modified silicone [*2] | — | 1.5 | 1.5 | — | 1.5 | 1.5 |
| Purified water | Balance | Balance | Balance | Balance | Balance | Balance |
| Total | 100 | 100 | 100 | 100 | 100 | 100 |

[*1] Amount to adjust pH to 10
[*2] KF-6005 (Shin-Etsu Chemical)

The above-described one-part hair dyes were each applied to the goat hair at 30° C. After it was caused to act on the hair for 20 minutes, the resulting goat hair was shampooed with an ordinarily used shampoo, followed by drying. As a result of the observation of the obtained color tone of the dyed hair, it was found that each composition had a good dyeing property and shampoo fastness.

Examples 7 to 11

Each cream-type first part component of two-part hair dyes shown in Table 2 and a second part component commonly used for the hair dyes shown in Table 3 were prepared in a conventional manner.

TABLE 2

| (wt. %) | Examples | | | | |
| --- | --- | --- | --- | --- | --- |
| | 7 | 8 | 9 | 10 | 11 |
| Azo dye (D-5) | 0.2 | 0.2 | 0.1 | 0.1 | 0.1 |
| Azo dye (D-9) | — | — | — | 0.1 | — |
| Azo dye (D-13) | — | 0.2 | — | — | 0.2 |
| Azo dye (D-20) | 0.1 | — | — | 0.2 | — |
| Azo dye (D-25) | — | 0.1 | — | — | — |
| Para-aminophenol | 0.3 | 0.1 | — | 0.1 | — |
| Toluene-2,5-diamine sulfate | 0.2 | — | 0.2 | — | 0.3 |
| 5-Aminoorthocresol | 0.1 | — | 0.2 | 0.1 | — |
| Meta-aminophenol | 0.2 | 0.1 | — | — | 0.3 |
| Ammonia (28 wt. %) | 8.0 | 8.0 | 8.0 | 8.0 | 8.0 |
| Stearyl alcohol | 8.0 | 8.0 | 8.0 | 8.0 | 8.0 |
| Coconut oil fatty acid monoethanolamide | 4.5 | 4.5 | 4.5 | 4.5 | 4.5 |
| Glyceryl stearate (SE) | 1.3 | 1.3 | 1.3 | 1.3 | 1.3 |
| Ceteareth-30 | 4.0 | 4.0 | 4.0 | 4.0 | 4.0 |
| Sodium lauryl sulfate | 1.0 | 1.0 | 1.0 | 1.0 | 1.0 |
| Oleic acid | 2.0 | 2.0 | 2.0 | 2.0 | 2.0 |
| 1,2-Propanediol | 1.5 | 1.5 | 1.5 | 1.5 | 1.5 |
| Polyether-modified silicone *3 | 1.5 | — | — | 1.5 | 1.5 |
| Protein hydrolysate | 0.5 | 0.5 | 0.5 | 0.5 | 0.5 |
| Panthenol | 0.8 | 0.8 | 0.8 | 0.8 | 0.8 |
| Tetrasodium edetate | 0.5 | 0.5 | 0.5 | 0.5 | 0.5 |
| Ammonium chloride *4 | q.s. | q.s. | q.s. | q.s. | q.s. |
| Purified water | Balance | Balance | Balance | Balance | Balance |
| Total | 100 | 100 | 100 | 100 | 100 |

*3 KF-6005 (Shin-Etsu Chemical)
*4 Amount to adjust pH to 10

TABLE 3

| (wt. %) | Common second part component |
| --- | --- |
| Cetanol | 2.0 |
| Sodium lauryl sulfate | 1.0 |
| Hydrogen peroxide (50 wt. %) | 12.0 |
| Methylparaben | 0.1 |
| Phosphoric acid | Amount to adjust the pH to 3.5 |
| Purified water | Balance |
| Total | 100.0 |

One part by weight of the first part component was mixed with 1 part by weight of the common second part component. The resulting mixture was applied to the goat hair at 30° C. and caused to act thereon for 30 minutes. The hair thus dyed was shampooed with an ordinarily employed shampoo, followed by drying. As a result of the observation of the obtained color tone of the hair, it was found that each composition had a good dyeing property and shampoo fastness.

The invention claimed is:

1. A hair dye composition comprising (1) an azo dye represented by the following formula (1):

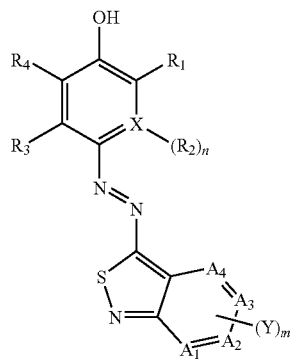

(wherein $R_1$, $R_2$, $R_3$, and $R_4$ each independently represents a hydrogen atom, an aliphatic hydrocarbon group, an aryl group, a halogen atom, an acyl group, a cyano group, an acylamino group, an aliphatic oxycarbonyl group, an aryloxycarbonyl group, a carbamoyl group, an aliphatic sulfonyl group, an arylsulfonyl group, a sulfamoyl group, an aliphatic oxycarbonylamino group, an aryloxycarbonylamino group, a sulfo group, a carboxy group, a carbamoylamino group, a sulfamoylamino group or an aliphatic or aromatic sulfonylamino group, wherein $R_1$ and $R_2$, and/or $R_3$ and $R_4$ may be coupled to form a 5- or 6-membered aromatic or non-aromatic ring; X represents a carbon atom or a nitrogen atom with the proviso that when X represents a carbon atom, n stands for 1, and when X represents a nitrogen atom, n stands for 0; $A_1$, $A_2$, $A_3$ and $A_4$ each independently represents a nitrogen atom or represents a carbon atom substituted by Y or having a hydrogen atom, with the proviso that at least one of $A_1$, $A_2$, $A_3$ and $A_4$ is a nitrogen atom; and Y represents a substituent with the proviso that m stands for an integer from 0 to 3), or a salt thereof, and (2) an oxidizing agent.

2. The hair dye composition according to claim 1, further comprising an oxidation dye.

3. A hair dyeing method comprising applying a hair dye composition to the hair, wherein the hair dye composition comprises an azo dye represented by the following formula (1):

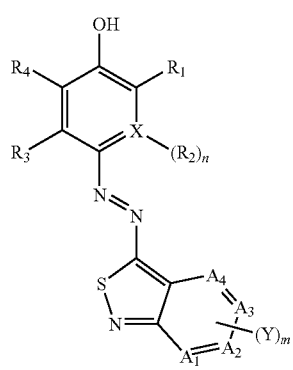

(1)

wherein $R_1$, $R_2$, $R_3$, and $R_4$ each independently represents a hydrogen atom, an aliphatic hydrocarbon group, an aryl group, a halogen atom, an acyl group, a cyano group, an acylamino group, an aliphatic oxycarbonyl group, an aryloxycarbonyl group, a carbamoyl group, an aliphatic sulfonyl group, an arylsulfonyl group, a sulfamoyl group, an aliphatic oxycarbonylamino group, an aryloxycarbonylamino group, a sulfo group, a carboxy group, a carbamoylamino group, a sulfamoylamino group or an aliphatic or aromatic sulfonylamino group, wherein $R_1$ and $R_2$, and/or $R_3$ and $R_4$ may be coupled to form a 5- or 6-membered aromatic or non-aromatic ring; X represents a carbon atom or a nitrogen atom with the proviso that when X represents a carbon atom, n stands for 1, and when X represents a nitrogen atom, n stands for 0; $A_1$, $A_2$, $A_3$ and $A_4$ each independently represents a nitrogen atom or represents a carbon atom substituted by Y or having a hydrogen atom, with the proviso that at least one of $A_1$, $A_2$, $A_3$ and $A_4$ is a nitrogen atom; and Y represents a substituent with the proviso that m stands for an integer from 0 to 3), or a salt thereof.

4. A hair dye composition comprising an azo dye represented by the following formula (2):

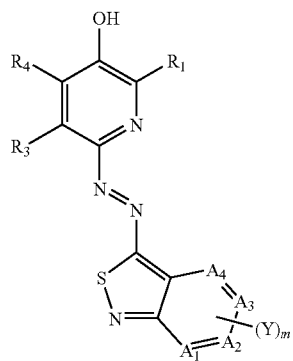

(2)

(wherein $R_1$, $R_3$, and $R_4$ each independently represents a hydrogen atom, an aliphatic hydrocarbon group, an aryl group, a halogen atom, an acyl group, a cyano group, an acylamino group, an aliphatic oxycarbonyl group, an aryloxycarbonyl group, a carbamoyl group, an aliphatic sulfonyl group, an arylsulfonyl group, a sulfamoyl group, an aliphatic oxycarbonylamino group, an aryloxycarbonylamino group, a sulfo group, a carboxy group, a carbamoylamino group, a sulfamoylamino group or an aliphatic or aromatic sulfonylamino group, wherein $R_3$ and $R_4$ may be coupled to form a 5- or 6-membered aromatic or non-aromatic ring; $A_1$, $A_2$, $A_3$ and $A_4$ each independently represents a nitrogen atom or represents a carbon atom substituted by Y or having a hydrogen atom, with the proviso that at least one of $A_1$, $A_2$, $A_3$ and $A_4$ is a nitrogen atom; and Y represents a substituent with the proviso that m stands for an integer from 0 to 3), or a salt thereof.

5. A hair dye composition comprising an azo dye represented by the following formula (1):

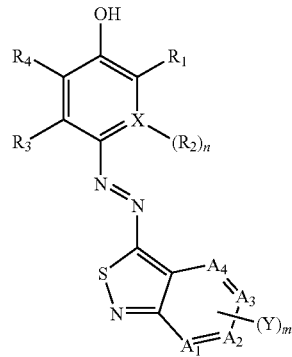

(1)

(wherein $R_1$, $R_2$, $R_3$, and $R_4$ each independently represents a hydrogen atom, an aliphatic hydrocarbon group, an aryl group, a halogen atom, an acyl group, a cyano group, an acylamino group, an aliphatic oxycarbonyl group, an aryloxycarbonyl group, a carbamoyl group, an aliphatic sulfonyl group, an arylsulfonyl group, a sulfamoyl group, an aliphatic oxycarbonylamino group, an aryloxycarbonylamino group, a sulfo group, a carboxy group, a carbamoylamino group, a sulfamoylamino group or an aliphatic or aromatic sulfonylamino group, wherein $R_1$ and $R_2$, and/or $R_3$ and $R_4$ may be coupled to form a 5- or 6-membered aromatic or non-aromatic ring; X represents a carbon atom or a nitrogen atom with the proviso that when X represents a carbon atom, n stands for 1, and when X represents a nitrogen atom, n stands for 0; $A_1$, $A_2$, $A_3$ and $A_4$ each independently represents a nitrogen atom or represents a carbon atom substituted by Y or having a hydrogen atom, with the proviso that at least two of $A_1$, $A_2$, $A_3$ and $A_4$ are nitrogen atoms; and Y represents a substituent with the proviso that m stands for an integer from 0 to 2), or a salt thereof.

6. The hair dye composition according to claim 4, further comprising an oxidation dye.

7. The hair dye composition according to claim 5, further comprising an oxidation dye.

8. The hair dye composition according to claim 1, wherein $R_1$ is chlorine or fluorine.

9. The hair dye composition according to claim 1, wherein $R_2$ is hydrogen.

10. The hair dye composition according to claim 1, wherein $R_3$ is hydrogen.

11. The hair dye composition according to claim 1, wherein $R_4$ is hydrogen.

12. The hair dye composition according to claim 1, wherein X is C.

13. The hair dye composition according to claim 1, wherein Y is cyano or alkylthio.

* * * * *